| United States Patent [19]
Franzmair | [11] 3,931,216
[45] Jan. 6, 1976 |

[54] PROCESS FOR THE MANUFACTURE OF 2-ARYLAMINO-2-IMIDAZOLINE DERIVATIVES AND THEIR SALTS

[75] Inventor: Rudolf Franzmair, Linz-Ebelsberg, Austria

[73] Assignee: Boehringer Ingelheim GmbH, Germany

[22] Filed: Mar. 29, 1974

[21] Appl. No.: 456,200

[30] Foreign Application Priority Data
Apr. 2, 1973   Germany............................ 2316377

[52] U.S. Cl............................. 260/309.6; 260/309.7
[51] Int. Cl.² .......................................... C07D 49/34
[58] Field of Search ................................. 260/309.6

[56] References Cited
UNITED STATES PATENTS

| | | | |
|---|---|---|---|
| 2,899,426 | 8/1959 | Bloom........................... | 260/309.6 X |
| 3,236,857 | 2/1966 | Zeile et al......................... | 260/309.6 |
| 3,462,433 | 8/1969 | Stahle et al................. | 260/309.6 X |
| 3,595,961 | 7/1971 | Stahle et al................. | 260/309.6 X |
| 3,752,810 | 8/1973 | Stahle et al................. | 260/309.6 X |

*Primary Examiner*—Ethel G. Love
*Attorney, Agent, or Firm*—Wenderoth, Lind & Ponack

[57] ABSTRACT

A process for the preparation of the known and valuable 2-aryl-amino-2-imidazoline derivatives which comprises condensing an appropriately substituted aniline with a 1-acyl-imidazolidin-2-one to produce an intermediate compound which on neutralisation in an aqueous medium is converted into a N-acyl derivative of the 2-aryl-amino-2-imidazoline, and splitting the intermediate compound or the said N-acyl derivative to give the corresponding free arylamino-2-imidazoline derivative or a salt thereof.

8 Claims, No Drawings

PROCESS FOR THE MANUFACTURE OF 2-ARYLAMINO-2-IMIDAZOLINE DERIVATIVES AND THEIR SALTS

This invention relates to a process for the preparation of 2-arylamino-2-imidazoline derivatives and the salts thereof.

It is known from Austrian Patent Specifications No. 248,428, 250,344 and 250,345, that 2-arylamino-2-imidazoline derivatives, especially the compound 2-(2′,6′-dichlorophenylamino)-2-imidazoline, possess a pronounced hypertensive action. It is also known, from Belgian Patent Specification No. 741,947, that this action is also possessed by acyl derivatives of the above-mentioned compounds; acyl derivatives are to be understood both as those which carry an acyl group on the aniline nitrogen atom and those in which the acyl group is allegedly bonded to the $N_1$ atom of the imidazoline ring.

Numerous processes for the preparation of these compounds are known. In most cases, these start from corresponding aniline derivatives, on the one hand, and from ethylenediamine, on the other, and are carried out via various intermediate products, which in most cases contain sulphur.

Thus, according to Austrian Patent Specification No. 248,428, the substituted aniline is first converted into the corresponding thiourea and the latter is converted into the isothiuronium salt, which is reacted with ethylenediamine, with cyclisation and elimination of mercaptan. However, this conversion, starting from 2,6-dichloroaniline, gives a yield of only about 15%, according to the example given in the patent specification.

In the direct reaction of the substituted phenylthiourea with ethylenediamine, with elimination of hydrogen sulphide and ammonia, as described in Austrian Patent Specification No. 250,344, the yield is even as low as about 5% if 2,6-dichloroaniline is used as the substituted aniline.

According to Austrian Patent Specification No. 250,345, it is also possible to condense a substituted phenylisothiocyanate with ethylenediamine, after which the resulting substituted N-phenyl-N′-(β-aminoethyl)-thiourea is cyclised. If 2,6-dichloroaniline is used as the substituted aniline in this process, the yield is 5 to 6%, relative to the substituted aniline, and here again the evolution of hydrogen sulphide has to be tolerated. Further processes are described in Austrian Patent Specifications No. 278,000, 278,776 and 284,838. These processes, in part, represent an improvement of the cyclisation of the substituted phenylisothiourea (Austrian Patent No. 278,000) but in part dispense with the use of compounds containing sulphur by employing substituted phenylguanidines (Austrian Patent No. 278,776) or appropriately substituted isocyanide-dihalide derivatives (Austrian Patent No. 284,838). In these processes, the yield, relative to the aniline derivative on which the product is based is admittedly higher, but is still only between 20 and 50% of theory. The acyl derivatives of these substituted 2-arylamino-2-imidazoline derivatives are obtained according to Belgian Patent Specification No. 741,947 by acylation of the corresponding arylamino-2-imidazolines, and according to the disclosure in this patent specification the acyl group is introduced either at the aniline nitrogen or at the imidazoline nitrogen depending on the nature of the arylimidazolines and on the reactivity of the acid halide used as the acylating agent.

It is a feature shared by all the above processes that the imidazoline radical is only formed by cyclisation after condensation with the aniline derivative. It has now been found, in contrast thereto, that the preparation of the known and valuable substituted 2-arylamino-2-imidazoline derivatives is possible in a substantially simpler manner and with incomparably better yields if the appropriately substituted aniline is condensed with a 1-acyl-imidazolidin-2-one, which produces, in a surprising reaction, intermediate products which on neutralisation in an aqueous medium are converted into N-acyl derivatives of the 2-arylamino 2-imidazolines. Both these intermediate products, which are more or less stable depending on the nature of the compound, and the N-acyl derivatives which may be prepared therefrom, surprisingly, may be split very easily, for example simply by boiling with an alcohol, to give the corresponding free arylamino-2-imidazolines, giving total yields, relative to aniline derivative, of more than 70% of theory.

Accordingly, the present invention provides a process for the preparation of a pharmacologically active 2-arylamino-2-imidazoline derivative having the general formula 1:

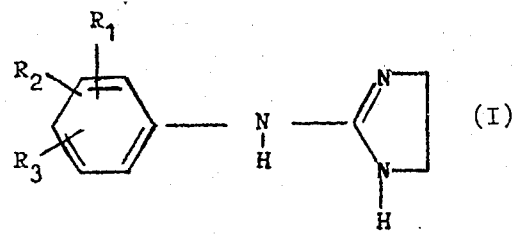

in which each of $R_1$, $R_2$ and $R_3$, which may be the same or different, is a hydrogen atom or a halogen atom, preferably chlorine or bromine, a lower alkyl or lower alkoxy group or the nitro group, with the proviso that in each case at least one of $R_1$, $R_2$ and $R_3$ is not a hydrogen atom, or of a salt thereof, which comprises reacting an aniline derivative having the general formula:

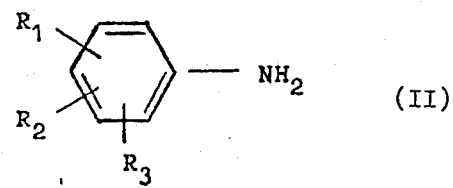

in which $R_1$, $R_2$ and $R_3$ are as defined above, with a 1-acylimidazolidin-2-one having the general formula:

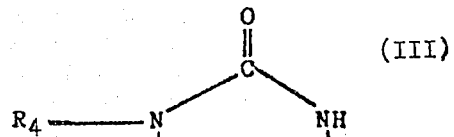

in which $R_4$ is the residue of an aliphatic or araliphatic carboxylic acid, which optionally may be substituted, or is an alkyl, aralkyl- or aryl-carbonic acid group, in the presence of at least 2 mols of phosphorus oxychloride per mol of the aniline derivative of the formula II which is employed, at a temperature from room temperature to at most the boiling point of phosphorus oxychloride, splitting the resulting intermediate product, after removal of the phosphorus oxychloride, or the acyl derivative of the compound of the formula (I) obtained by neutralisation thereof, by treatment with an alcohol, acid or an alkaline compound for more than one hour and isolating the resulting compound of the formula (I) as the free bases or a salt thereof with an inorganic or organic acid.

The nature of aryl-radical $R_4$ is not important for the success in reaction. As a rule, the residues of aliphatic acid and alkyl carbonic acids may not have more than 10, preferably not more than 4 C-atoms, the cycloaliphatic carboxylic acids between 4 and 7 C-atoms and the araliphalic residues in araliphatic acids are benzyl and phenethyl. Higher acids are much more expensive.

Preferably, the aniline derivatives of the formula (II and the 1-acylimidazolidin-2-one are employed in approximately equimolar amounts. It is also possible to use either of the reactants in slight excess, for example from 10 to 20% by weight, relative to the amount of the other reactant. In principle, the reaction will also take place if a substantially greater excess is used, but certain losses of yield, for example a reduction of the yield to about 75%, must be expected because of interfering side-reactions.

Suitably, at least 3 mols of phosphorus oxychloride are employed per mol of aniline derivative of the formula (II), because in this way optimum purity of the end product of the formula (I) is achieved. The simultaneous use of phosphorus oxychloride as the solvent for the reactants is particularly preferred. However, the reaction also may be carried out in an inert organic solvent, for example in a chlorinated hydrocarbon, as the reaction medium.

After completion of the reaction, it is desirable to remove the excess phosphorus oxychloride and this is preferably done by distilling it off. The acid evaporation residue then contains an intermediate product containing phosphorus, which in most cases cannot be isolated and on treatment with cold water, for example ice water, and even more rapidly on treatment with an aqueous alkaline medium such as, for example, an aqueous solution of sodium carbonate or sodium hydroxide, is split to give the corresponding acyl derivative of the compound of formula (1). This neutralisation may be effected both by direct addition of the aqueous medium to the evaporation residue or by dissolving the latter in an organic solvent such as, for example methylene chloride, and treating the solution with optionally ice-cooled water or an alkaline solution.

The acyl derivatives of the formula I, which are obtained in the form of a solid on neutralisation, are homogeneous well-crystallised products of sharp melting point, the structure of which is difficult to determine unambiguously. On the basis of the IR-spectrum and NMR-spectrum, in most cases it can be assumed that the acyl group is bonded to one of the two nitrogen atoms in the imidazoline ring and not to the aniline nitrogen, in contrast to most of the compounds which are described in Belgian Patent No. 741,947 and which are stated there, with few exceptions, to be compounds which carry the acyl group on the aniline nitrogen. In some cases, for example in the case of the acetyl and phenacetyl compound of 2-(2',6'-dichlorophenylamino)-imidazoline, yet a further, more readily soluble acetyl or phenacetyl derivative may be isolated in addition, in substantially smaller amounts, from the mother liquor, and this compound also carries the acyl group bonded to an imidazoline nitrogen. These two acetyl or phenacetyl derivatives which are found are, according to the IR-spectrum and NMR-spectrum and $P_k$-values, not identical with the acetyl or phenacetyl derivatives of 2-(2',6'-dichlorophenylamino)-imidazoline obtained according to the process of Belgian Patent Specification No. 741,947, though there the phenacetyl derivative is allotted a different structure from the acetyl derivative. The more sparingly soluble acyl derivatives which represent the main products of the process according to the invention may be easily split to give the compounds of formula (I), this being essential to the invention. These acyl derivatives of the compounds of formula (I) all also show, though to different extents, a blood pressure-lowering and central-depressant action, such as is known from the compounds of formula (I).

The splitting off of the acyl group in order to provide compounds of formula I is achievable both with acids, namely inorganic acids or organic acids such as, for example, acetic acid, or with alkaline reagents, such as sodium hydroxide solution, potassium hydroxide solution, sodium carbonate, ammonia, primary, secondary or tertiary amines such as alkylamines, for example n-butylamine, ethanolamine, benzylamine or piperidine, or alkali metal alcoholates. In some cases, the agent used for the splitting reaction can act without the use of a solvent or diluent, for example where splitting is carried out with dilute acids or alkalis or with organic amines. In cases where the splitting agent is solid or the compound of the formula I, with $R_3$ not equal to hydrogen, is inadequately soluble, it is advisable to add a suitable solvent or diluent. In most cases it is advisable to carry out the saponification under warm conditions, for example at a temperature from 60° to 120°C, suitably at the boiling point of the reaction medium, in order to avoid excessively long reaction times. The duration of heating in such cases is mostly in excess of 1 hour and suitably several hours.

Surprisingly, it has been found that the splitting off of the acyl radical may be effected with a lower aliphatic alcohol, and in particular preferably with primary alcohols, and takes place particularly favourably. As a rule it is advisable to dissolve the acyl compound in the alcohol and to boil the solution under reflux. Using this procedure, the splitting reaction is very gentle, the yield is over 90% and practically no byproducts result.

For the success of the process according to the invention it is not necessary to prepare the acyl compounds. It suffices if the excess phosphorus oxychloride is removed from the condensation reaction product by distillation, after which the splitting agent is added directly to the evaporation residue which contains the intermediate product containing phosphorus. The end product obtained after the splitting has taken place is nevertheless obtained in a completely pure form and the total yield relative to the aniline derivative of the formula (II) may be increased yet further thereby.

This "one-pot reaction" has proved particularly successful for the manufacture of the known active compound 2-(2',6'-dichlorophenylamino)-2-imidazoline, which has become accessible particularly simply, and in better yields than hitherto, by this new process.

The reaction products may be isolated either directly as the base or, after acidification, in the form of a salt. If, for example, the splitting off of the acyl group is effected with an acid, the salt, for example the hydrochloride, in many cases precipitates as crystals from the aqueous solution and may be obtained immediately in the pure state by filtration.

The 1-acyl-imidazolidin-2-ones of the formula (III) used as the starting material are new, with few exceptions. They may be obtained by acylation of ethyleneurea in one step, with yields of up to 80%.

The following Examples illustrate the process according to the invention in more detail.

EXAMPLE 1

217.3g of 1-acetyl-imidazolidin-2-one (10% excess) are stirred with 250g of 2,6-dichloroaniline and 2,245 ml of $POCl_3$ for 68 hours at 50°C. $POCl_3$ is stripped off as completely as possible in vacuo, 10 kg of ice are added to the residue and the mixture is rendered alkaline with 25% strength sodium hydroxide solution whilst cooling with ice. It is then extracted three times with $CH_2Cl_2$ and the combinded extracts are washed once with 1 N NaOH and twice with $H_2O$, dried and evaporated to dryness in vacuo; yield of 1-acetyl-2-(2',-6'-dichlorophenylamino)-2-imidazoline, 403.0 g, representing 92.5% of theory, relative to 2,6-dichloroaniline.

Recrystallisation from toluene gives 337.0 g of the pure 1-acetyl compound (80.3% of theory of melting point 164-167°C).

Analysis (calculated + 0.1 mol of $H_2O$) $C_{11}H_{11}Cl_2N_3O$; calculated: C 48.24; H 4.12; N 15.34; O 6.42; Cl 25.88, found: C 48.4; H 4.1; N 15.1; O 6.3; Cl 25.7

1-Acetyl-imidazolidin-2-one, used as the starting material, is obtained by acetylation of ethyleneurea by boiling in acetic anhydride.

Melting point: 184°–186°C.

337.0 g of the 1-acetyl compound in 4 l of $CH_3OH$ are boiled for 6 hours under reflux. The methanol is stripped off in vacuo, the brownish oily residue is dissolved in 1.3 l of ethanol, about 2 g of active charcoal are added and the mixture is stirred for 10 minutes at room temperature, and filtered. The filtrate is cooled to 0°, 20% strength alcoholic HCl is added dropwise whilst stirring (300 ml), and the precipitation is then completed by means of 1.8 l of ether. The mixture is stirred for a further 20 minutes at 0° and filtered and the product is washed with ethanol/ether and dried.

Yield: 313.1 g (that is to say 94.9% of theory) of 2-(2',6'-dichlorophenylamino)-2-imidazoline hydrochloride.

Total yield relative to 2,6-dichloroaniline is, accordingly, 76.2% of theory. Melting point: 304°–310°C (decomposition).

Analysis (calculated assuming 0.1 mol of $H_2O$) $C_9H_9Cl_2N_3 \cdot HCl$; calculated: C 40.28; H 3.82; N 15.66; O 0.61; Cl 39.63; C 40.4; H 3.7; N 15.7; O 0.7 (=Δ); Cl 39.5.

EXAMPLE 2

544.3 mg (2 mols) of the 1-acetyl compound prepared according to Example 1, in 8 ml of 1 N hydrochloric acid, are heated under reflux for 4.5 hours, brought to room temperature and left to stand at this temperature for 16 hours, whereupon crystals are obtained. These are filtered off, washed with a little water and dried.

Yield: 355 mg of 2-(2',6'-dichlorophenylamino)-2-imidazoline hydrochloride, that is to say 66.5% of theory.

Melting point: 304°–310°C (decomposition)

EXAMPLE 3

5.0 g of the 1-acetyl compound, prepared according to Example 1, are boiled in ethanol for 15 hours under reflux. The mixture is evaporated in vacuo, 25 ml of ethanol are added and the resulting solution is cooled to 0°. Alcoholic hydrochloric acid is added to this solution until the mixture reacts acid, the hydrochloride is precipitated with 25 ml of ether, the mixture is left to stand for 2.5 hours at room temperature and is then filtered and the product is washed with ethanol/ether and dried.

Yield: 3.80 g of 2-(2',6'-dichlorophenylamino)-2-imidazoline hydrochloride, that is to say 77% of theory.

Melting point: 304°–310°C (decomposition)

EXAMPLE 4

5.0 g of the 1-acetyl compound according to Example 1 in 50 ml of n-butanol are kept at 95°C for 15 hours. After working up as described in Example 3, 4.18 g of 2-(2',6'-dichlorophenylamino)-2-imidazoline hydrochloride, that is to say 84.8% of theory, are obtained.

Melting point: 304°–310°C (decomposition)

EXAMPLE 5

0.23 g of Na are dissolved in 100 ml of $CH_3OH$, 2.72 g of the 1-acetyl compound according to Example 1 are added thereto and the mixture is left to stand for 16 hours at room temperature. The methanol is stripped off completely in vacuo, water is added to the residue, the mixture is extracted three times with $CH_2Cl_2$ and the $CH_2Cl_2$ phase is washed with $H_2O$ until neutral, dried over $Na_2SO_4$ and evaporated. The oily residue is dissolved in 15 ml of ethanol and 20% strength alcoholic hydrochloric acid is added until the mixture reacts strongly acid. After addition of 100 ml of ether, crystallisation occurs. The mixture is left to stand for 3 hours at room temperature and filtered, and the crystals are washed with ethanol/ether and with ether, and dried. 2.36 g of 2-(2',6'-dichlorophenylamino)-2-imidazoline hydrochloride (88.5% of theory) are thus obtained.

Melting point: 304°–310°C (decomposition)

The substance is obtained in an analytically pure form.

EXAMPLE 6

2.72 g of the 1-acetyl compound according to Example 1, in 50% strength acetic acid, are heated for 4 hours under reflux and the mixture is then evaporated completely. The residue is dissolved in 5 ml of ethanol, ethanolic hydrochloric acid is added until the mixture reacts strongly acid, 50 ml of ether are then added and the mixture is left to stand for some time at room temperature. It is then filtered and the crystals are washed with ether and dried. 2.55 g of 2-(2',6'-dichlorophenylamino)-2-imidazoline.HCl, that is to say 95.9% of theory, are thus obtained.

The substance is analytically pure.

EXAMPLE 7

1.0 g of the 1-acetyl compound according to Example 1 is dissolved in 15 ml of piperidine and the solution is boiled for 22 hours under reflux. It is then evaporated to dryness. 15 ml of absolute toluene are added twice to the residue and the mixture is evaporated in each case. The resulting crystalline residue is dissolved in 10 ml of ethanol, the solution is cooled to 0°, 20% strength ethanolic hydrochloric acid is added until the mixture reacts strongly acid, the hydrochloride is precipitated by adding 12 ml of ether and the whole is left for some time at 0°C. The crystals are filtered off, washed with a little ethanol/ether and dried. Yield of 2-(2',6'-dichlorophenylamino)-2-imidazoline hydrochloride: 882 mg (that is to say 90.8% of theory) of melting point: 304°–310°C. The material is analytically pure.

EXAMPLE 8

8.1 g of 2,6-dichloroaniline and 7.05 g of 1-acetylimidazolidin-2-one in 72.8 ml of $POCl_3$ are stirred for 72 hours at 50°C. The excess $POCl_3$ is distilled off in vacuo, the oily residue is dissolved in 500 ml of $CH_3OH$ and the solution is concentrated to about 100 ml in vacuo and boiled under reflux for 3 hours. The mixture is then cooled to room temperature, 400 ml of ether are added slowly whilst stirring, the whole is left to stand for some time at room temperature and the crystals are filtered off, washed with ethanol/ether and with ether and dried.

Yield of 2-(2',6'-dichlorophenylamino)-2-imidazoline hydrochloride 10.5 g, that is to say 78.8% of theory.

Melting point: 304°–310°C (decomposition)

EXAMPLE 9

8.1 g of 2,6-dichloroaniline and 9.45 g of 1-carboethoxy-imidazolidin-2-one (melting point: 123°–126°C) (10% excess) in 74 ml of $POCl_3$ are stirred for 60 hours at 50°C. The excess $POCl_3$ is then distilled off in vacuo and the viscous residue is introduced into a mixture of 70 ml of 40% strength NaOH and 500 g of ice. The resulting solution is extracted three times with ether/ethyl acetate and the organic phases are washed until neutral, dried over $Na_2SO_4$ and evaporated. 14.46 g of a viscous oil are obtained, and are dissolved in 200 ml of methanol, and the solution is boiled for 6 hours under reflux. The methanol is stripped off in vacuo, the resinous residue is dissolved in 50 ml of hot ethanol, the solution is cooled to 0°C and 11 ml of 21% strength ethanolic hydrochloric acid are added. the hydrochloride is precipitated with 100 ml of ether, the mixture is left at 0°C for one-half hour and then filtered and the product is washed with ethanol/ether and dried.

Yield: 10.46 g of 2-(2',6'-dichlorophenylamino)-2-imidazoline hydrochloride, that is to say 78.6% of theory.

Melting point: 304°–310°C. The material is analytically pure.

1-Carboethoxy-imidazolidin-2-one, used as the starting material, is obtained by acylation of ethyleneurea with chlorocarbonic acid ethyl ester in pyridine at 60°C. Melting point: 124°–126°C.

EXAMPLE 10

16.2 g of 2,6-dichloroaniline and 15.63 g of 1-propionyl-imidazolidin-2-one (10% excess) in 146 ml of $POCl_3$ are kept at 50°C for 70 hours, whilst stirring.

The excess $POCl_3$ is then distilled off in vacuo and ice/$H_2O$ is added to the residue until it has dissolved completely. The solution is then rendered alkaline with 4 N NaOH whilst cooling with ice, and is extracted four times with ethyl acetate. The organic phase is washed until neutral, dried over $Na_2SO_4$ and evaporated. The colourless residue is dissolved in 100 ml of hot isopropanol and the solution is cooled, whereupon colourless crystals separate out. These are filtered off, washed with a little isopropanol and dried. Yield of the propionyl derivative of 2-(2',6'-dichlorophenylamino)-2-imidazoline = 24.6 g, that is to say 86.0% of theory.

Melting point: 143°–146°C.

Analysis: $C_{12}H_{13}Cl_2N_3O$; calculated: C 50.37; H 4.58; N 14.68; O 5.59; Cl 24.78; found: C 50.4; H 4.7; N 14.8; O 5.8; Cl 24.5

1-Propionyl-imidazolidin-2-one, used as the starting material, is obtained by reaction of ethyleneurea with propionic anhydride at the boil. It has a melting point of 151°–154°C.

6.0 g of this propionyl compound in 100 ml of $CH_3OH$ are heated to the reflux temperature for 5.5 hours. The solvent is evaporated to dryness in vacuo, the colourless resinous residue is dissolved in 30 ml of hot ethanol, the solution is cooled to 0°C, 5 ml of 20% strength ethanolic hydrochloric acid are added and the resulting precipitation of the hydrochloride is completed by means of 70 ml of ether. The product is filtered off, washed with ethanol/ether and with ether and dried.

Yield of 2-(2',6'-dichlorophenylamino)-2-imidazoline. HCl = 4.95 g, that is to say 88.8% of theory.

The substance is obtained in an analytically pure form.

EXAMPLE 11

16.3 g of 2,6-dichloroaniline and 17.18 g of 1-n-butyrylimidazolidin-2-one (10% excess) are reacted with 146 ml of $POCl_3$, entirely analogously to Example 10, and worked up. Yield of the butyryl derivative of 2-(2',6'-dichlorophenylamino)-2-imidazoline = 23.95 g, that is to say 80% of theory.

For analysis, the product is recrystallised from cyclohexane and dried for 8 hours at 80°C and 0.1 mm Hg.

Melting point: 107°–108°C

Analysis: $C_{13}H_{15}Cl_2N_3O$ calculated: C 52.01; H 5.03; N 13.99; O 5.32; Cl 23.62 found: C 52.3; H 5.1; N 13.7; O 5.3; Cl 23.9

1-n-Butyrylimidazolidin-2-one, used as the starting material, was obtained by reaction of ethyleneurea with n-butyric anhydride in pyridine under reflux. Melting point: 98°–102°C.

25.0 g of this butyryl compound in 150 ml of $CH_3OH$ are boiled for 6 hours. The mixture is worked up analogously to Example 10. Yield of 2-(2',6'-dichlorophenylamino)-2-imidazoline hydrochloride = 17.65 g, that is to say 80% of theory.

EXAMPLE 12

16.2 g of 2,6-dichloroaniline and 24.2 g of 1-benzyloxycarbonyl-imidazolidin-2-one are reacted in 146 ml of $POCl_3$ analogously to Example 10, and worked up.

Yield: 34.0 g of the benzyloxycarbonyl derivative of 2-(2',6'-dichlorophenylamino)-2-imidazoline, that is to say 93.6% of theory, in the form of a viscous resin which does not crystallise. A picrate is prepared from a small amount of this resin. Melting point: 193°–200°C Analysis: $C_{23}H_{20}Cl_2N_6O_9$; calculated: C 46.40; H 3.38; N 14.11; O 24.18; Cl 11.91; found: C 46.7; H 3.1; N 14.3; O 24.0; Cl 12.0

1-Benzyloxycarbonyl-imidazolidin-2-one, employed as the starting material, is obtained by reaction of ethyleneurea with carbobenzoxy chloride in pyridine at room temperature. Melting point: 188°–190°C 33.0 g of this benzyloxycarbonyl compound are split with methanol as described in Example 10 and worked up. Analytically pure 2-(2′,6′-dichlorophenylamino-2-imidazoline. HCl of melting point: 304°–310°C (decomposition) is obtained.

EXAMPLE 13

8.1 g of 2,6-dichloroaniline are reacted with 11.30 g of 1-phenylacetyl-imidazolidin-2-one (10% excess) in 73 ml of $POCl_3$, as described in Example 10, and worked up.

Yield: 15.0 g of 1-phenylacetyl-2-(2′,6′-dichlorophenylamino)-2-imidazoline of melting point: 170°C = 78% of theory.

Analysis: $C_{17}H_{15}Cl_2N_3O$; calculated: C 58.63; H 4.34; N 12.07; O 4.59; Cl 20.36; found: C 59.0; H 4.3; N 12.0; O 4.3; Cl 20.5

1-Phenyl-acetyl-imidazolidin-2-one, used as the starting material, is obtained by reaction of ethyleneurea with phenylacetyl chloride and antipyrine, by melting the substances together at 90°C.

Melting point: 112°–114°C.

5.00 g of this 1-phenylacetyl compound in 50 ml of methanol are boiled for 17 hours under reflux. The mixture is worked up as described in Example 12.

Yield: 3.6 g of 2-(2′,6′-dichlorophenylamino)-2-imidazoline.HCl, that is to say 94.7% of theory, analytically pure.

EXAMPLE 14

3.48 g of this 1-phenylacetyl compound, prepared according to Example 13, in 50 ml of n-butylamine are boiled under reflux for 5 hours. The mixture is then completely evaporated in vacuo; 20 ml of benzene are added twice to the residue and the mixture is in each case evaporated to dryness. The colourless, crystalline residue is dissolved in 25 ml of ethanol, 20% strength alcoholic hydrochloric acid is added in the cold, 50 ml of ether are then added and the mixture is kept at 0°C for some time. The crystals are then filtered off, washed with ethanol/ether and dried.

Yield: 2.54 g of 2-(2′,6′-dichlorophenylamino)-2-imidazoline.HCl, that is to say 92.1% of theory; analytically pure.

EXAMPLE 15

16.2 g of 2,6-dichloroaniline and 17.2 g of 1-isobutyrylimidazolidin-2-one are reacted with 146 ml of $POCl_3$ as described in Example 10, and worked up. Recrystallisation of the resulting crude product from i-propanol gives 27.6 g (90.0% of theory).

Melting point of the isobutyryl derivative of 2-(2′,6′-dichlorophenylamino)-2-imidazoline, thus obtained: 162°–164°C (sublimation from 110°C onwards).

Analysis: $C_{13}H_{15}Cl_2N_3O$; calculated: C 52.01; H 5.04; Cl 23.62; N 13.99; O 5.32; found: C 52.4; H 5.1; Cl 23.6; N 13.7; O 5.2

1-Isobutyryl-imidazolidin-2-one, used as the starting material, is prepared by reaction of ethyleneurea with isobutyric acid chloride and antipyrine at 90°C. Melting point: 110°–112°C.

EXAMPLE 16

3.2 g of 2,6-dichloroaniline and 3.4 g of 1-cyclopropylcarbonyl-imidazolidin-2-one in 29 ml of $POCl_3$ are reacted as in Example 10, and worked up.

Yield: 5.15 g of the cyclopropylcarbonyl derivative of 2-(2′,6′-dichlorophenylamino)-2-imidazoline, that is to say 86.4% of theory; from i-propanol. Melting point: 147°–149°C Analysis: $C_{13}H_{13}Cl_2N_3O$ (calculated + 0.1 mol of water); calculated: C 52.08; H 4.43; Cl 23.65; N 14.02; O 5.87; found: C 52.2; H 4.4; Cl 23.7; N 13.9; O 6.0

1-Cyclopropylcarbonyl-imidazolidin-2-one, used as the starting material, is prepared by reaction of cyclopropylcarboxylic acid chloride with ethyleneurea in pyridine at room temperature. Melting point: 147°–154°C.

1.49 g of the cyclopropylcarbonyl compound thus obtained, in 30 ml of methanol, are boiled under reflux for 25 hours. The mixture is then worked up as described in Example 10.

Yield: 1.15 g of 2-(2′,6′-dichlorophenylamino)-2-imidazoline.HCl, that is to say 83% of theory, of analytically pure material.

EXAMPLE 17

8.1 g of 2,6-dichloroaniline and 11.1 g of 1-phenoxyacetyl-imidazolidin-2-one in 75 ml of $POCl_3$ are stirred at 80°C. The mixture is then evaporated in vacuo, the residue is dissolved in methylene chloride and added dropwise at 0°C to a solution of 80 g of potassium bicarbonate in 500 ml of water, whilst stirring. The phases are then separated, the aqueous phase is additionally extracted twice with methylene chloride and the combined organic phases are washed with water until neutral, dried and evaporated. The crystalline residue is recrystallised from a very small amount of acetonitrile.

Yield of the phenoxyacetyl derivative of 2-(2′,6′-dichlorophenylamino)-2-imidazoline = 15.36 g, that is to say 84.5% of theory. Melting point: 175°–178°C.

Analysis: ($C_{17}H_{15}Cl_2N_3O_2$; 364.239) calculated assuming 0.3 ml of water; calculated: C 55.26; H 4.25; N 11.37; O 9.95; Cl 19.18; found: C 54.8; H 4.3; N 11.4; O 9.8; Cl 19.4

1-Phenoxyacetyl-imidazolidin-2-one, used as the starting material, can be prepared by reaction of ethyleneurea with phenoxyacetyl chloride at 130°, without a solvent. Melting point: 188°–190°C.

2.0 g of the phenoxyacetyl compound thus obtained are reacted with 40 ml of methanol as described in Example 10, and worked up.

Yield: 1.23 g of 2-(2′,6′-dichlorophenylamino)-2-imidazoline.HCl, that is to say 88.2% of theory, of analytically pure material.

EXAMPLE 18

16.2 g of 2,6-dichloroaniline and 20.62 g of 1-carbophenoxy-imidazolidin-2-one in 146 ml of $POCl_3$ are reacted as described in Example 16, and worked up.

Yield: 29.1 g of 1-carbophenoxy-2-(2′,6′-dichlorophenylamino)-2-imidazoline, that is to say 83% of theory. Melting point 152°–155°C.

Analysis: $C_{16}H_{13}Cl_2N_3O_2$; calculated: C 54.87; H 3.74; Cl 20.24; N 12.00; O 9.13; found: C 55.2; H 3.8; Cl 20.2; N 11.9; O 9.3

1-Carbophenoxy-imidazolidin-2-one, used as the starting material, is prepared by reaction of ethyleneurea with chlorocarbonic acid phenyl ester and antipyrine at 90°C. Melting point: 175°–183°C.

3.5 g of 1-carbophenoxy-2-(2',6'-dichlorophenylamino)-2-imidazolidine in a mixture of 25 ml of dioxane and 25 ml of 10% strength acetic acid are boiled for 6 hours under reflux. The mixture is then evaporated in vacuo. The residue is dissolved in water and the solution is rendered alkaline with 4 N NaOH and extracted with ether. The ether phase is washed with a little water until neutral, dried over sodium sulphate and evaporated. The colourless crystals are dissolved in ethanol, the solution is cooled to 0°C and acidified with alcoholic hydrochloric acid, and the incipient crystallisation is completed by means of approx. 50 ml of ether. The product is filtered off, washed with ethanol/ether and dried. Yield: 2.20 g. that is to say 83% of theory. The material is analytically pure.

EXAMPLE 19

8.1 g of 2,4-dichloroaniline (0.05 mol) and 7.8 g of 1-propionyl-imidazolidin-2-one in 72 ml of $POCl_3$ are stirred for 73 hours at 60°C. The $POCl_3$ is then removed in vacuo, the residue is dissolved in 80 ml of methylene chloride, 80 g of ice are added and the mixture is shaken vigorously for 30 minutes. It is then rendered alkaline with 40% strength sodium hydroxide solution and shaken for a further 10 mins. and the phases are separated. The aqueous phase is additionally extracted twice with methylene chloride and the combined methylene chloride phases are washed with water until neutral, dried over sodium sulphate and evaporated. 12.33 g of the propionyl derivative of 2-(2',4'-dichlorophenylamino)-2-imidazoline, that is to say 86.2% of theory, are obtained as a crystalline residue. For analysis, the product is recrystallised from i-propanol. Melting point: 129°–131°C.

Analysis: ($C_{12}H_{13}Cl_2N_3O$; 286.167); calculated: C 50.37; H 4.58; N 14.68; O 5.59; Cl 24.78; found: C 50.5; H 4.5; N 14.4; O 5.8; Cl 24.5

2.86 g (0.01 mol) of this propionyl compound, in 30 ml of methanol, are boiled for 13 hours under reflux. The mixture is then evaporated in vacuo, whereupon 2.30 g, that is to say 88.5% of theory, of 2-(2',4'-dichlorophenylamino)-2-imidazoline are obtained in a crystalline residue. For analysis, the material is recrystallised from a little toluene. Melting point: 138°–139°C.

Analysis: ($C_9H_9Cl_2N_3$; 230.102); calculated: C 46.98; H 3.97; N 18.24; Cl 30.81; found: C 46.6; H 3.9; N 17.8; Cl 30.9

EXAMPLE 20

12.75 g of o-chloroaniline and 14.09 g of 1-acetylimidazolidin-2-one in 144 ml of $POCl_3$ are stirred for 71 hours at 60°C. The mixture is worked up as described in Example 19 and 15.45 g, that is to say 65.3%, of the acetyl derivative of 2-(2'-chlorophenylamino)-2-imidazoline are obtained as a crystalline product, which, for analysis, is recrystallised from i-propanol and toluene. Melting point: 142°–143°C Analysis: ($C_{11}H_{12}ClN_3O$; 237.688); calculated: C 55.59; H 5.08; N 17.68; O 6.73; Cl 14.92; found: C 55.7; H 5.1; N 17.5; O 7.3; Cl 14.6

2.37 g of the acetyl compound in 30 ml of methanol are boiled for 13 hours under reflux. The reaction mixture is evaporated in vacuo and 1.80 g (92.3% of theory) of 2-(2'-chlorophenylamino)-2-imidazoline are obtained as a crystalline residue. For analysis, this is recrystallised from toluene. Melting point: 130°–133°

Analysis: ($C_9H_{10}ClN_3$, 195.650); calculated: C 55.25; H 5.17; Cl 18.11; found: C 55.1; H 5.2; Cl 18.2

EXAMPLE 21

5.02 g of 2,6-dibromoaniline and 2.82 g of 1-acetylimidazolidin-2-one in 36 ml of $POCl_3$ are stirred for 66 hours at 70°C. The $POCl_3$ is removed in vacuo, the residue is dissolved in 70 ml of methylene chloride, about 70 g of ice are added, the mixture is shaken for 45 minutes, 40% strength sodium hydroxide solution is added whilst also adding a further 30 g of ice and the whole is shaken for 15 minutes. The phases are separated, the aqueous phase is additionally extracted twice with methylene chloride and the combined organic phases are washed with water until neutral, dried over sodium sulphate and evaporated. 7.13 g of crystalline residue are obtained and are recrystallised from isopropanol.

Yield 5.56 g (77.1% of theory) of 1-acetyl-2-(2',6'-dibromophenylamino)-2-imidazoline. Melting point: 182°–185°C.

Analysis: ($C_{11}H_{11}Br_2N_3O$; 361.050) calculated assuming 0.1 mol of water; calculated: C 36.41; H 3.09; N 11.58; O 4.86; Br 44.05; found: C 36.3; H 3.0; N 11.2; O 4.9; Br 44.2

1.80 g of 1-acetyl-2-(2',6'-dibromophenylamino)-2-imidazoline in 20 ml of methanol are boiled for 6 hours under reflux. The mixture is then evaporated, the residue is dissolved in 15 ml. of hot ethanol, the solution is cooled to 0°C and 1.5 ml of 20% strength ethanolic hydrochloric acid and 20 ml of ether are added. The resulting precipitate is filtered off and washed with ethanol/ether.

Yield 1.50 g (84.6% of theory) of 2-(2',6'-dibromophenylamino)-2-imidazoline.HCl.

The material is analytically pure. Melting point: 301°–306°C (with decomposition).

Analysis: ($C_9H_{10}Br_2ClN_3$; 355.460); calculated: C 30.42; N 2.84; N 11.82; Cl 9.98; found: C 30.6 N 2.9; N 11.5; Cl 9.9

EXAMPLE 22

13.81 g of o-nitroaniline and 14.09 g of 1-acetylimidazolidin-2-one in 144 ml of $POCl_3$ are stirred for 69 hours at 50°C. The excess $POCl_3$ is removed in vacuo, the residue is dissolved in 200 ml of methylene chloride, 100 g of ice are added and the mixture is shaken for 15 minutes. A further 50 g of ice are then added, the mixture is rendered alkaline with 40% strength sodium hydroxide solution and stirred for 30 minutes, and the phases are separated. The aqueous phase is additionally extracted twice with methylene chloride and the combined organic phases are washed with water until neutral, dried over sodium sulphate and evaporated. The residue (21.28 g) is triturated with ethyl acetate, left for 1 hour at room temperature, filtered off and washed with ethyl acetate.

Yield: 13.09 g of the acetyl derivative of 2-(2'-nitrophenylamino)-2-imidazoline, that is to say 53.1% of theory. For analysis, the compound is recrystallised from methyl ethyl ketone. Melting point: 175°C Analysis: ($C_{11}H_{12}N_4O_3$; 248.244); calculated: C 53.23; H 4.88; N 22.57; O 19.33; found: C 53.5; H 4.9; N 22.4; O 19.1

2.48 g of the acetyl compound in 50 ml of methanol are boiled for 8 hours under reflux. The mixture is then evaporated completely in vacuo. The yellow crystalline residue, which is 2-(2'-nitrophenylamino)-2-imidazoline, is recrystallised from toluene. Melting point: 165°–169°C.

Analysis: ($C_9H_{10}N_4O_2$; 206.206); calculated: C 52.41; H 4.88; N 27.16; O 15.55; found: C 52.5; H 5.0; N 27.4; O 15.3

EXAMPLE 23

12.1 g of 2,6-dimethylaniline and 14.09 g of 1-acetylimidazolidin-2-one are stirred with 145 ml of $POCl_3$ for 16 hours at 50°C. The excess $POCl_3$ is removed in vacuo, the residue is dissolved in 300 ml of methylene chloride and the solution is slowly added dropwise, whilst stirring vigorously, to a suspension of 70 g of sodium bicarbonate in 300 ml of water. After completion of the dropwise addition, the mixture is stirred for a further 1.5 hours, the phases are then separated, the aqueous phase is additionally extracted three times with methylene chloride and the combined organic phases are washed twice with water, dried over sodium sulphate and evaporated. The residue (18.81 g) in 150 ml of methanol is boiled under reflux for 32 hours, the mixture is evaporated to dryness and the residue is triturated with ether, filtered off, washed with ether and dried.

Yield 9.15 g (48.4% of theory) of 2-(2',6'-dimethylphenylamino)-2-imidazoline For analysis, the material is recrystallised from benzene:cyclohexane (2:3). Melting point: 155°–156°C Analysis: ($C_{11}H_{15}N_3$; 189.243); calculated: C 69.82; H 7.99; N 22.19; found: C 69.8; H 8.0; N 22.2

EXAMPLE 24

14.1 g of 2-chloro-6-methyl-aniline, 14.09 g of 1-acetyl-imidazolidin-2-one and 146 ml of $POCl_3$ are stirred for 70 hours at 50°C and evaporated in vacuo, methylene chloride is added to the residue, and the whole is shaken with 100 g of ice for 30 minutes. The mixture is then rendered alkaline with 40% strength sodium hydroxide solution and extracted three times with methylene chloride (a total of 700 ml), and the methylene chloride solution is washed with water until neutral, dried over sodium sulphate and evaporated. The residue is dissolved in 250 ml of warm ether and insoluble matter is filtered off. The ether solution is extracted with three times 70 ml and twice 40 ml of 2% strength acetic acid and is then rendered alkaline with 4 N NaOH and cooled, and the resulting crystals are filtered off, washed with water and dried.

Yield: 15.6 g of the acetyl derivative of 2-(2'-chloro-6'-methylphenylamino)-2-imidazoline, that is to say 62.1% of theory. For analysis, the material is recrystallised from a little isopropanol and dried over silica gel at 80° and 0.01 mm Hg.

Analysis: ($C_{12}H_{14}N_3OCl$; 251.715); calculated: C 57.26; H 5.61; N 16.68; O 6.37; Cl 14.08; found: C 57.6; H 5.7; N 16.7; O 6.1; Cl 14.1

5.04 g of the acetyl compound, in methanol, are boiled under reflux for 10 hours and the crystalline residue is recrystallised from i-propanol.

Yield : 3.29 g of 2-(2'-chloro-6'-methylphenylamino)-2-imidazoline, that is to say 78.9% of theory. Melting point: 143°–146°C.

Analysis: ($C_{10}H_{12}N_3Cl$); calculated: C 57.33; H 5.77; N 20.00; Cl 16.90; found: C 57.1; H 5.9; N 19.8; Cl 16.9

EXAMPLE 25

15.6 g of 1-propionyl-imidazolidin-2-one and 12.3 g of o-anisidine in 146 ml of $POCl_3$ are stirred for 71 hours at 50°C. The brown solution is evaporated in vacuo, the residue is taken up in methylene chloride and the mixture is shaken with ice for 30 minutes. It is then rendered alkaline with 40% strength sodium hydroxide solution, the phases are separated and the aqueous phase is additionally extracted with twice 400 ml of methylene chloride. The combined methylene chloride solutions are washed with cold-saturated sodium chloride solution, dried over sodium sulphate and evaporated. The red-coloured, partially crystalline residue is dissolved in 300 ml of hot isopropanol, and the solution is filtered hot, and is cooled. The resulting crystals are filtered off and dried.

Yield: 11.7 g of the propionyl derivative of 2-(2'-methoxyphenylamino)-2-imidazolidine, that is to say 47.4% of theory. Melting point: 158°–164°C.

Analysis: ($C_{13}H_{17}N_3O_2$; 247.300), calculated assuming 0.2 mol of $H_2O$; calculated: C 62.25; H 6.99; N 16.75; O 14.02; found: C 62.2; H 7.0; N 16.6; O 13.9

4.94 g of the propionyl compound in methanol, are boiled under reflux for 12 hours. The residue is dissolved in 10 ml of hot ethanol, alcoholic hydrochloric acid is added until the solution reacts acid, and 10 ml of ether are then added, whereupon crystals separate out.

Yield: 2.30 g of 2-(2'-methoxyphenylamino)-2-imidazoline, that is to say 51% of theory.

The crystals are taken up in chloroform and the solution is thoroughly shaken once with dilute sodium hydroxide solution, washed with water until neutral, dried over sodium sulphate and evaporated. The colourless residue is boiled up in approx. 100 ml of cyclohexane, the mixture is cooled and filtered and the product is washed with cyclohexane. For analysis, it is recrystallised from benzene:cyclohexane (1:1). Melting point: 120°–122°C Analysis: ($C_{10}H_{13}N_3O$; 191.235); calculated: C 62.82; H 6.85; N 21.98; O 8.37; found: C 62.8; H 6.9; N 21.9; O 8.7

What is claimed is:

1. A process for the preparation of 2-arylamino-2-imidazoline derivatives selected from the group consisting of compounds of the formula

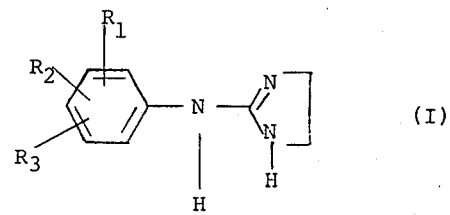

(I)

in which each of $R_1$, $R_2$ and $R_3$, which may be the same or different, is selected from the group consisting of hydrogen, chlorine, bromine, alkyl with 1–4 C-atoms, alkoxy with 1–4 C-atoms and nitro, with the proviso that in each case at least one of $R_1$, $R_2$ and $R_3$ is not a hydrogen atom, or acid addition salt thereof, which comprises reacting aniline derivatives of the formula

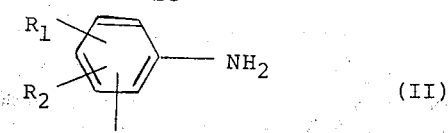

in which $R_1$, $R_2$ and $R_3$ are as defined above, with 1-acrylimidazolidin-2-ones of the formula

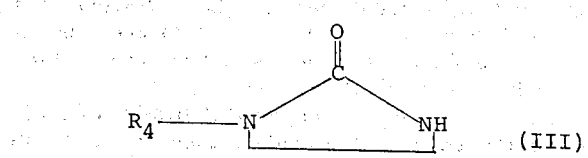

in which $R_4$ is selected from the group consisting of the residues of aliphatic-cycloaliphatic- and araliphatic monocarboxylic acids, alkyl-carbonic-, aralkylcarbonic and aryl-carbonic acids, in the presence of at least 2 mols of phosphorus oxychloride per mol of the aniline derivative of the formula (II) at a temperature from room temperature to at most the boiling point of phosphorus oxychloride, neutralizing the resulting phosphorus containing intermediate product to give an acyl derivative of the compounds of formula I, whereby acyl is $R_4$ and splitting off the acyl group in said acyl derivative by treating it with splitting agent selected from the group consisting of lower aliphatic monoalcohols, inorganic acids, organic acids, alkaline sodium salts, alkaline potassium salts, ammonia, amines and alkalialcoholates for more than one hour and recovering said compound of formula I directly as the base or acidifying said base and recovering it as an acid addition salt.

2. A process according to claim 1, in which more than 3 mols of phosphorus oxychloride are used per mol of aniline derivative of formula (II).

3. A process according to claim 1, in which the reaction is carried out in excess phosphorus oxychloride as the solvent.

4. A process according to claim 1, in which in the said acyl derivative of the compound of formula I the acyl group is split off by treating said acyl product with a lower aliphatic primary alcohol with boiling for more than 1 hour.

5. A process according to claim 1, in which in the said acyl derivative of the compound of formula I the acyl group is split off by boiling the said acyl product with methanol for more than 1 hour.

6. A process according to claim 1 in which 2,6-dichloroaniline is reacted with the acylimidazolin-2-one of formula III.

7. A process according to claim 1 in which the phosphorus containing intermediate product as such is treated with said splitting agent for more than 1 hour.

8. The process according to claim 1 wherein the splitting agent is acetic acid, sodium hydroxide, potassium hydroxide, sodium carbonate, ammonia, n-butylamine, ethanolamine, benzylamine, piperidine or an alkali metal alcoholate.

* * * * *